(12) United States Patent
Hildebrand et al.

(10) Patent No.: US 6,923,814 B1
(45) Date of Patent: Aug. 2, 2005

(54) SYSTEM AND METHODS FOR CERVICAL SPINAL FUSION

(75) Inventors: Bryan D. Hildebrand, Whitefish, MT (US); Patrick Miles, San Diego, CA (US); Scot Martinelli, San Diego, CA (US); Jared Arambula, San Diego, CA (US); Matthew Curran, Carlsbad, CA (US); Eric Kovach, Carlsbad, CA (US); Troy Woolley, San Diego, CA (US); Jeff Castleberry, Escondido, CA (US)

(73) Assignee: Nuvasive, Inc., San Diego, CA (US)

( * ) Notice: Subject to any disclaimer, the term of this patent is extended or adjusted under 35 U.S.C. 154(b) by 0 days.

(21) Appl. No.: 10/283,429

(22) Filed: Oct. 29, 2002

Related U.S. Application Data

(60) Provisional application No. 60/336,501, filed on Oct. 30, 2001.

(51) Int. Cl.[7] ............................................. A61B 17/88
(52) U.S. Cl. ....................................................... 606/99
(58) Field of Search ........................... 606/99, 104, 61, 606/205, 206, 207; 623/17.11, 17.16; 600/104, 600/106, 137; 24/326, 335, 350, 502, 504, 24/505, 515, 516, 518; 269/47, 48, 49, 60, 269/77, 78, 87.3, 91, 98, 100, 108, 188, 189, 269/217, 218, 256, 261, 264

(56) References Cited

U.S. PATENT DOCUMENTS

| | | | | |
|---|---|---|---|---|
| 803,692 A | * | 11/1905 | Hill | 81/113 |
| 3,486,505 A | * | 12/1969 | Morrison | 606/90 |
| 3,518,993 A | * | 7/1970 | Blake | 606/142 |
| 3,604,487 A | * | 9/1971 | Gilbert | 81/443 |
| 3,745,995 A | | 7/1973 | Kraus | 128/82.1 |
| 3,848,601 A | | 11/1974 | Ma et al. | 128/305 |
| 4,026,304 A | | 5/1977 | Levy | 128/419 |
| 4,026,305 A | | 5/1977 | Brownlee et al. | 128/419 |
| 4,646,738 A | | 3/1987 | Trott | 606/170 |
| 4,657,550 A | | 4/1987 | Daher | 623/17 |
| 4,743,256 A | | 5/1988 | Brantigan | 623/17 |
| 4,781,591 A | | 11/1988 | Allen | |
| 4,834,757 A | | 5/1989 | Brantigan | |
| 4,877,020 A | * | 10/1989 | Vich | 606/86 |
| 4,878,915 A | | 11/1989 | Brantigan | 623/17 |
| 4,932,975 A | | 6/1990 | Main et al. | 623/17 |
| 4,961,740 A | | 10/1990 | Ray et al. | 606/61 |
| 4,962,766 A | | 10/1990 | Herzon | 128/741 |
| 5,026,373 A | | 6/1991 | Ray et al. | 606/61 |

(Continued)

FOREIGN PATENT DOCUMENTS

| CA | 2015507 | 1/1991 |
|---|---|---|

(Continued)

OTHER PUBLICATIONS

Alleyne, Cargill H., et al., "Current and future approaches to lumbar disc surgery: A literature review", *Medscape Orthopedics & Sports Medicine, 1*, [www.medscape.com/Medscape/OrthoSportsMed/1997/v01.n11/.../mos3057],(1997).

(Continued)

*Primary Examiner*—Eduardo C. Robert
*Assistant Examiner*—David Comstock
(74) *Attorney, Agent, or Firm*—Jonathan Spangler

(57) ABSTRACT

A system for performing spinal fusion between adjacent cervical vertebrae, including an implant and an introducer system, and related methods.

7 Claims, 13 Drawing Sheets

U.S. PATENT DOCUMENTS

| | | |
|---|---|---|
| 5,055,104 A | 10/1991 | Ray .............................. 606/61 |
| 5,062,845 A | 11/1991 | Kuslich et al. ............... 606/80 |
| 5,092,572 A | 3/1992 | Litwak et al. .............. 269/328 |
| 5,133,717 A | 7/1992 | Chopin ......................... 606/61 |
| 5,133,755 A | 7/1992 | Brekke ......................... 623/16 |
| 5,171,278 A | 12/1992 | Pisharodi ..................... 623/17 |
| 5,192,327 A * | 3/1993 | Brantigan ................ 623/17.11 |
| 5,217,497 A | 6/1993 | Mehdian ...................... 623/17 |
| 5,269,785 A | 12/1993 | Bonutti ........................ 606/80 |
| 5,284,153 A | 2/1994 | Raymond et al. ........... 128/741 |
| 5,290,494 A | 3/1994 | Coombes et al. ............. 264/41 |
| 5,300,076 A | 4/1994 | Leriche ........................ 606/73 |
| 5,304,210 A | 4/1994 | Crook .......................... 607/51 |
| 5,306,307 A | 4/1994 | Senter et al. ................. 623/17 |
| 5,306,309 A * | 4/1994 | Wagner et al. .......... 623/17.16 |
| 5,322,505 A | 6/1994 | Krause et al. ................ 604/24 |
| 5,334,205 A | 8/1994 | Cain |
| 5,336,223 A | 8/1994 | Rogers ......................... 606/61 |
| 5,364,400 A | 11/1994 | Rego, Jr. et al. ............. 606/72 |
| 5,395,372 A | 3/1995 | Holt et al. .................... 606/61 |
| 5,397,363 A | 3/1995 | Gelbard ....................... 623/17 |
| 5,405,391 A | 4/1995 | Henderson et al. ........... 623/17 |
| 5,413,602 A | 5/1995 | Metz-Stavenhagen ........ 623/17 |
| 5,425,772 A | 6/1995 | Brantigan .................... 623/17 |
| 5,431,658 A | 7/1995 | Moskovich ................... 606/99 |
| 5,443,514 A | 8/1995 | Steffee ......................... 623/17 |
| 5,443,515 A | 8/1995 | Cohen et al. ................. 623/17 |
| 5,445,639 A | 8/1995 | Kuslich et al. ............... 606/80 |
| 5,454,811 A | 10/1995 | Huebner ...................... 606/60 |
| 5,458,638 A | 10/1995 | Kuslich et al. ............... 623/17 |
| 5,484,403 A | 1/1996 | Yoakum et al. ............... 604/59 |
| 5,489,308 A * | 2/1996 | Kuslich et al. .......... 623/17.11 |
| 5,514,180 A * | 5/1996 | Heggeness et al. ...... 623/17.16 |
| 5,522,879 A | 6/1996 | Scopelianos ................... 623/1 |
| 5,522,899 A | 6/1996 | Michelson .................... 623/17 |
| 5,524,624 A | 6/1996 | Tepper et al. ............. 128/660.3 |
| 5,527,312 A | 6/1996 | Ray .............................. 606/61 |
| 5,534,030 A | 7/1996 | Navarro et al. ............... 623/17 |
| 5,540,688 A | 7/1996 | Navas .......................... 606/61 |
| 5,545,222 A | 8/1996 | Bonutti ........................ 623/11 |
| 5,562,736 A | 10/1996 | Ray et al. ..................... 623/17 |
| 5,565,005 A | 10/1996 | Erickson et al. .............. 607/51 |
| 5,571,190 A | 11/1996 | Ulrich et al. ................. 623/17 |
| 5,571,192 A | 11/1996 | Schonhoffer ................. 623/17 |
| 5,593,409 A | 1/1997 | Michelson .................... 606/61 |
| 5,609,636 A | 3/1997 | Kohrs et al. .................. 623/17 |
| 5,611,800 A | 3/1997 | Davis et al. .................. 606/61 |
| 5,611,810 A * | 3/1997 | Arnold et al. ............... 606/185 |
| 5,632,747 A | 5/1997 | Scarborough et al. ........ 606/79 |
| 5,645,598 A | 7/1997 | Brosnahan .................... 623/17 |
| 5,653,761 A | 8/1997 | Pisharodi ..................... 623/17 |
| 5,653,762 A | 8/1997 | Pisharodi ..................... 623/17 |
| 5,658,336 A | 8/1997 | Pisharodi ..................... 623/17 |
| 5,658,337 A | 8/1997 | Kohrs et al. .................. 623/17 |
| 5,662,710 A | 9/1997 | Bonutti ........................ 623/11 |
| 5,665,122 A | 9/1997 | Kambin ....................... 623/17 |
| 5,669,909 A | 9/1997 | Zdeblick et al. .............. 606/61 |
| 5,676,703 A | 10/1997 | Gelbard ....................... 623/17 |
| 5,683,394 A | 11/1997 | Rinner ......................... 606/86 |
| 5,683,400 A * | 11/1997 | McGuire ...................... 606/96 |
| 5,683,464 A | 11/1997 | Wagner et al. ................ 623/17 |
| 5,690,629 A | 11/1997 | Asher et al. .................. 606/61 |
| 5,700,264 A | 12/1997 | Zucherman et al. .......... 606/79 |
| 5,700,291 A | 12/1997 | Kuslich et al. ............... 623/17 |
| 5,700,292 A | 12/1997 | Marguiles .................... 623/17 |
| 5,702,449 A | 12/1997 | McKay ................... 623/17.16 |
| 5,702,451 A | 12/1997 | Biedermann et al. ......... 623/17 |
| 5,702,453 A | 12/1997 | Rabbe et al. ................. 623/17 |
| 5,702,454 A | 12/1997 | Baumgartner ................ 623/17 |
| 5,702,455 A | 12/1997 | Saggar .................... 623/17.15 |
| 5,703,451 A | 12/1997 | Yamamichi ................. 318/492 |
| 5,707,373 A * | 1/1998 | Sevrain et al. ................ 606/72 |
| 5,711,957 A | 1/1998 | Patat et al. .................. 424/224 |
| 5,716,415 A * | 2/1998 | Steffee .................... 623/17.16 |
| 5,720,748 A | 2/1998 | Kuslich et al. ............... 606/80 |
| 5,720,751 A * | 2/1998 | Jackson ........................ 606/86 |
| 5,728,159 A * | 3/1998 | Stroever et al. ........... 623/23.5 |
| 5,741,261 A | 4/1998 | Moskovitz et al. ........... 606/79 |
| 5,755,797 A | 5/1998 | Baumgartner ................ 623/17 |
| 5,766,252 A * | 6/1998 | Henry et al. ............. 623/17.16 |
| 5,772,661 A | 6/1998 | Michelson .................... 606/61 |
| 5,775,331 A | 7/1998 | Raymond et al. ........... 128/741 |
| 5,779,642 A | 7/1998 | Nightengale ................ 600/461 |
| 5,782,830 A * | 7/1998 | Farris .......................... 606/61 |
| 5,782,919 A | 7/1998 | Zdeblick et al. .............. 623/17 |
| 5,785,710 A | 7/1998 | Michelson .................... 606/61 |
| 5,797,909 A | 8/1998 | Michelson .................... 606/61 |
| 5,800,549 A | 9/1998 | Bao et al. ..................... 623/17 |
| 5,800,550 A | 9/1998 | Sertich ......................... 623/17 |
| 5,814,084 A | 9/1998 | Grivas et al. ................. 623/16 |
| 5,851,208 A | 12/1998 | Trott ............................ 606/80 |
| 5,865,845 A * | 2/1999 | Thalgott .................. 623/17.16 |
| 5,865,848 A | 2/1999 | Baker ........................... 623/17 |
| 5,885,299 A | 3/1999 | Winslow et al. .............. 606/99 |
| 5,888,219 A | 3/1999 | Bonutti ........................ 623/11 |
| 5,888,224 A | 3/1999 | Beckers et al. ............... 623/17 |
| 5,893,890 A | 4/1999 | Pisharodi ..................... 623/17 |
| 5,904,719 A | 5/1999 | Errico et al. .................. 623/17 |
| 5,910,315 A | 6/1999 | Stevenson et al. .......... 424/422 |
| 5,954,769 A | 9/1999 | Rosenlicht ................... 623/16 |
| 5,968,098 A | 10/1999 | Winslow ...................... 623/17 |
| 5,993,474 A * | 11/1999 | Ouchi ......................... 606/206 |
| 6,004,326 A | 12/1999 | Castro et al. ................. 606/99 |
| 6,008,433 A * | 12/1999 | Stone ...................... 623/20.14 |
| 6,015,436 A | 1/2000 | Schunhuffer ................. 623/17 |
| 6,033,405 A | 3/2000 | Winslow et al. .............. 606/61 |
| 6,039,761 A | 3/2000 | Li et al. ....................... 623/17 |
| 6,042,582 A | 3/2000 | Ray ............................. 606/61 |
| 6,045,580 A | 4/2000 | Scarborough et al. ........ 623/17 |
| 6,048,342 A | 4/2000 | Zucherman et al. .......... 606/61 |
| 6,063,088 A | 5/2000 | Winslow ...................... 606/61 |
| 6,083,225 A | 7/2000 | Winslow et al. .............. 606/61 |
| 6,096,080 A | 8/2000 | Nicholson et al. ............ 623/17 |
| 6,102,948 A | 8/2000 | Brosnahan, III ............. 623/17 |
| 6,120,506 A * | 9/2000 | Kohrs et al. .................. 606/80 |
| 6,132,472 A | 10/2000 | Bonutti ........................ 623/23 |
| 6,159,211 A | 12/2000 | Boriani et al. ................ 606/61 |
| 6,159,215 A * | 12/2000 | Urbahns et al. .............. 606/86 |
| 6,193,756 B1 | 2/2001 | Studer et al. ............. 623/17.15 |
| 6,200,347 B1 | 3/2001 | Anderso .................. 623/16.11 |
| 6,224,607 B1 * | 5/2001 | Michelson .................... 606/96 |
| 6,224,631 B1 | 5/2001 | Kohrs ...................... 623/17.11 |
| 6,241,769 B1 | 6/2001 | Nicholson et al. ........ 623/17.11 |
| 6,241,771 B1 * | 6/2001 | Gresser et al. ............ 623/17.16 |
| 6,251,140 B1 | 6/2001 | Marino et al. ............ 623/17.16 |
| 6,258,125 B1 | 7/2001 | Paul et al. ................ 623/17.11 |
| 6,277,149 B1 | 8/2001 | Boyle et al. .............. 623/17.16 |
| 6,319,257 B1 * | 11/2001 | Carignan et al. ............. 606/99 |
| 6,371,989 B1 | 4/2002 | Chauvin et al. ......... 623/17.11 |
| 6,383,221 B1 * | 5/2002 | Scarborough et al. ... 623/17.11 |
| 6,440,142 B1 * | 8/2002 | Ralph et al. .................. 606/99 |
| 6,442,814 B1 | 9/2002 | Landry et al. ................. 26/29 |
| 6,454,806 B1 | 9/2002 | Cohen et al. ............. 623/17.15 |
| 6,527,773 B1 | 3/2003 | Lin et al. ...................... 606/61 |
| 6,547,823 B2 * | 4/2003 | Scarborough et al. ... 623/17.16 |
| 6,595,998 B2 | 7/2003 | Johnson et al. .............. 606/90 |
| 6,626,905 B1 * | 9/2003 | Schmiel et al. ............... 606/61 |
| 6,635,086 B2 * | 10/2003 | Lin .......................... 623/17.11 |
| 6,648,895 B2 * | 11/2003 | Burkus et al. ................ 606/90 |
| 6,755,841 B2 * | 6/2004 | Fraser et al. .................. 606/99 |
| 2002/0058950 A1 * | 5/2002 | Winterbottom et al. ....... 606/99 |
| 2003/0105528 A1 | 6/2003 | Shimp et al. |

FOREIGN PATENT DOCUMENTS

| | | |
|---|---|---|
| EP | 369603 | 5/1990 |
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| WO | WO-94/04100 | 3/1994 |
| WO | WO-94/10928 | 5/1994 |
| WO | WO-95/01810 | 1/1995 |
| WO | WO-96/08205 | 3/1996 |
| WO | WO-96/17564 | 3/1996 |
| WO | WO-96/41582 | 12/1996 |
| WO | WO-97/20513 | 6/1997 |
| WO | WO-97/33525 | 9/1997 |
| WO | WO-97/37620 | 10/1997 |
| WO | WO-98/09586 | 3/1998 |
| WO | WO-98/14142 | 4/1998 |
| WO | WO-98/17208 | 4/1998 |
| WO | WO-98/25539 | 6/1998 |
| WO | WO-99/08627 | 2/1999 |
| WO | WO-99/38461 | 8/1999 |
| WO | WO-00/45712 | 8/2000 |
| WO | WO-00/45713 | 8/2000 |
| WO | WO-91/06261 | 5/2001 |
| WO | WO-01/41681 | 6/2001 |
| WO | WO-01/49333 | 7/2001 |

OTHER PUBLICATIONS

Benini, et al., "Undercutting decompression and posterior fusion with translaminar facet screw fixation in degenerative lumbar spinal stenosis: Technique and results", *Neuro-Orthopedics*, (1995), 159-172.

Kambin, et al., "History and current status of percutaneous arthroscopic disc surgery", *Spine, 21,* (1996),57S-61S.

Stein, et al., "Percutaneous facet joint fusion: Preliminary experience", *Journal of Vascular and Interventional Radiology, 4,* (1993), 69-74.

Vamvanij, et al., "Surgical treatment of internal disc disruption: An outcome study of four fusion techniques", *Journal of Spinal Disorders, 4,* (1998),375-382.

\* cited by examiner

5 X 11 X 11mm DEPICTED

5 X 14 X 11mm DEPICTED

5 X 14 X 14mm DEPICTED

SYSTEM AND METHODS FOR CERVICAL SPINAL FUSION

CROSS-REFERENCE TO RELATED APPLICATION

This application claims the benefit of the filing date under 35 USC 119(e) of provisional application entitled "Spinal Surgery Systems and Methods", Ser. No. 60/336,501 filed Oct. 30, 2001, and fully incorporated herein by reference.

BACKGROUND OF THE INVENTION

I. Field of the Invention

The present invention relates to spinal surgery and, more particularly, to systems and methods for performing spinal fusion between adjacent cervical vertebrae.

II. Discussion of the Prior Art

Intervertebral spinal inserts are used to provide support and maintain normal distance between adjacent vertebrae in cases where a patient's vertebral discs have degenerated. Such degeneration can occur as a result of aging or trauma and typically results in pinched or damaged nerves between or proximal to the adjacent vertebrae. Moreover, such disc degeneration causes shifting of the loading along the patient's spinal column, which in turn further accelerates the vertebral degeneration.

Intervertebral inserts are typically used to reestablish normal intervertebral spacing and to cause fusion between adjacent vertebral bodies. A common problem with the existing intervertebral spinal inserts is that they do not provide stabilization in two perpendicular directions in the plane of the patient's intervertebral space. Another disadvantage is that, during such major surgery, the actual insertion of the intervertebral insert requires distraction of the adjacent vertebrae to first open a sufficiently large passage for the insertion of the insert therebetween. Such distraction is typically performed by dedicated instrumentation and invasive tools, which must first enter the intervertebral space and then grip and hold apart the adjacent vertebrae. Moreover, the shape of current inserts does not take advantage of the natural contoured shape of the adjacent vertebral surfaces.

It is desirable to be able to insert one or more prosthetic implants between vertebrae to stabilize the vertebrae and promote fusion of the vertebrae. Further, it is desirable to insert these implants via a minimally invasive procedure to reduce the potential trauma to a patient. In minimally invasive implant insertion procedures, it is desirable to be able to monitor the location of the implant relative to the vertebrae using a fluoroscope. When implanting bony implants, however, it may be difficult to visualize the implant in this fashion. A need exists, therefore, for an inserter, implant, and minimally invasive procedure that enables a surgeon to monitor the implant location relative to the vertebrae during the insertion process.

The present invention is directed at addressing this need and eliminating, or at least reducing, the effects of the shortcomings of the prior art as described above.

SUMMARY OF THE INVENTION

The present invention overcomes the drawbacks of the prior art by providing, according to a first broad aspect of the present invention, a system for performing spinal fusion, including a spinal implant and an implant insertion tool. The spinal implant has top and bottom sides, lateral sides, a proximal side and a distal side, where the top and bottom sides each have a generally polygonal cross-section. The proximal side is intersected generally perpendicular by at least two apertures defining a purchase region therebetween. The implant insertion tool includes an elongate fork member and a generally tubular lock member. The elongate fork member has a pair of clamping arms extending generally parallel and away from the distal end of an elongate section. Each clamping arm has an engagement feature dimensioned to slidably engage the apertures of the spinal implant. A thread feature is provided at the proximal end of the elongate section, as well as a handling feature further proximal from the thread feature. The generally tubular lock member has a distal end, a bore dimensioned to receive a proximal portion of the elongate fork member therethrough from the distal end but smaller than the outer dimension of said clamping arms of the elongate fork member, and a thread feature at the proximal end dimensioned to engage the thread feature of the elongate fork member. Clockwise rotation of the tubular lock member with respect to the elongate fork member causes the distal end of the tubular lock member to force the clamping arms of the elongate fork member to displace laterally toward the longitudinal axis of the elongate fork member. This causes the engagement features to displace toward each other, securing the spinal implant by creating a compressive force on the purchase region when the engagement features are slidably engaged in the at least two apertures.

The present invention overcomes the drawbacks of the prior art by providing, according to a second broad aspect of the present invention, a spinal implant for use with an inserter having an elongate fork member and a tubular lock member and at least two engagement features. The spinal implant includes a generally annular portion of bone fusion matrix having top and bottom sides, lateral sides, a proximal side and a distal side, with the top and bottom sides having a generally polygonal cross-section. At least two apertures are provided generally perpendicular to and intersecting with the proximal side, creating a purchase region therebetween.

The present invention overcomes the drawbacks of the prior art by providing, according to a third broad aspect of the present invention, an implant insertion device for inserting a spinal implant having at least two apertures defining a purchase region therebetween. The implant insertion device includes an elongate fork member and a generally tubular lock member. The elongate fork member has a pair of clamping arms extending generally parallel and away from the distal end of an elongate section. Each clamping arm has an engagement feature dimensioned to slidably engage the apertures of the spinal implant. A thread feature is provided at the proximal end of the elongate section. A generally cylindrical handling feature is provided further proximal from the thread feature. The generally tubular lock member has a distal end, a bore dimensioned to receive a proximal portion of the elongate fork member therethrough from the distal end but smaller than the outer dimension of the clamping arms of the elongate fork member. A thread feature is provided at the proximal end dimensioned to engage the thread feature of the elongate fork member. Clockwise rotation of the tubular lock member with respect to the elongate fork member will cause the distal end of said tubular lock member to force the clamping arms of the elongate fork member to displace laterally toward the longitudinal axis of the elongate fork member. This lateral displacement causes the engagement features to displace toward each other and thus secure the spinal implant by creating a compressive force on the purchase region.

The present invention overcomes the drawbacks of the prior art by providing, according to a fourth broad aspect of the present invention, a method for performing spinal fusion, comprising the steps of: (a) providing a spinal implant having top and bottom sides, lateral sides, a proximal side and a distal side, said top and bottom sides having a generally polygonal shape, the proximal side being intersected generally perpendicular by at least two apertures creating a purchase region therebetween; (b) providing a spinal implant insertion device having an elongate fork member and a tubular lock member, the elongate fork member having a pair of clamping arms extending generally parallel and away from the distal end of an elongate section, each clamping arm having an engagement feature dimensioned to slidably engage the apertures of the spinal implant, a thread feature at the proximal end of the elongate section and a handling feature further proximal from the thread feature, and the generally tubular lock member having a distal end, a bore dimensioned to receive a proximal portion of the elongate fork member therethrough from the distal end but smaller than the outer dimension of the clamping arms of the elongate fork member, and a thread feature at the proximal end that is dimensioned to engage the thread feature of the elongate fork member; (c) engaging the at least two apertures of the spinal implant with the engagement features of the elongate fork member; (d) rotating the tubular lock member clockwise with respect to the elongate fork member causing the distal end of said tubular lock member to force the clamping arms of the elongate fork member to displace laterally toward the longitudinal axis of the elongate fork member, the lateral displacement causing the engagement features to displace toward each other and thus securing the spinal implant by creating a compressive force on the purchase region; (d) introducing the inserter and the secured spinal implant into a prepared intervertebral space; (e) rotating the tubular lock member counterclockwise with respect to the elongate fork member causing a reduction of the compressive force on the purchase region and allowing the engagement features of the elongate fork member to be slidably disengaged from the spinal implant; and (f) removing the spinal implant insertion device from the prepared intervertebral space.

BRIEF DESCRIPTION OF THE DRAWINGS

Other objects and advantages of the invention will become apparent upon reading the following detailed description and upon reference to the drawings in which.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with apparatus-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The apparatus disclosed herein boast a variety of inventive features and components that warrant patent protection, both individually and in combination.

Figure 1:
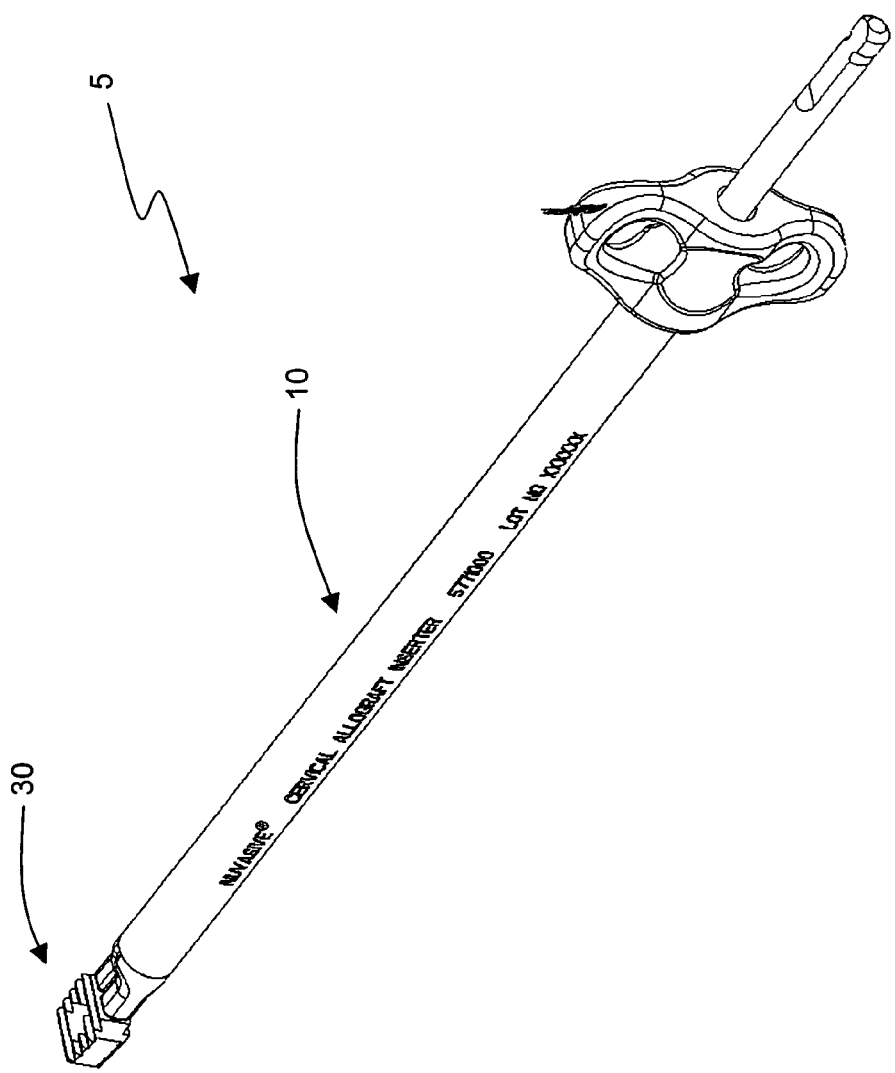
FIG. 1 is a perspective view of a system for performing cervical spinal fusion according to a first broad aspect of the present invention.
Figure 2:
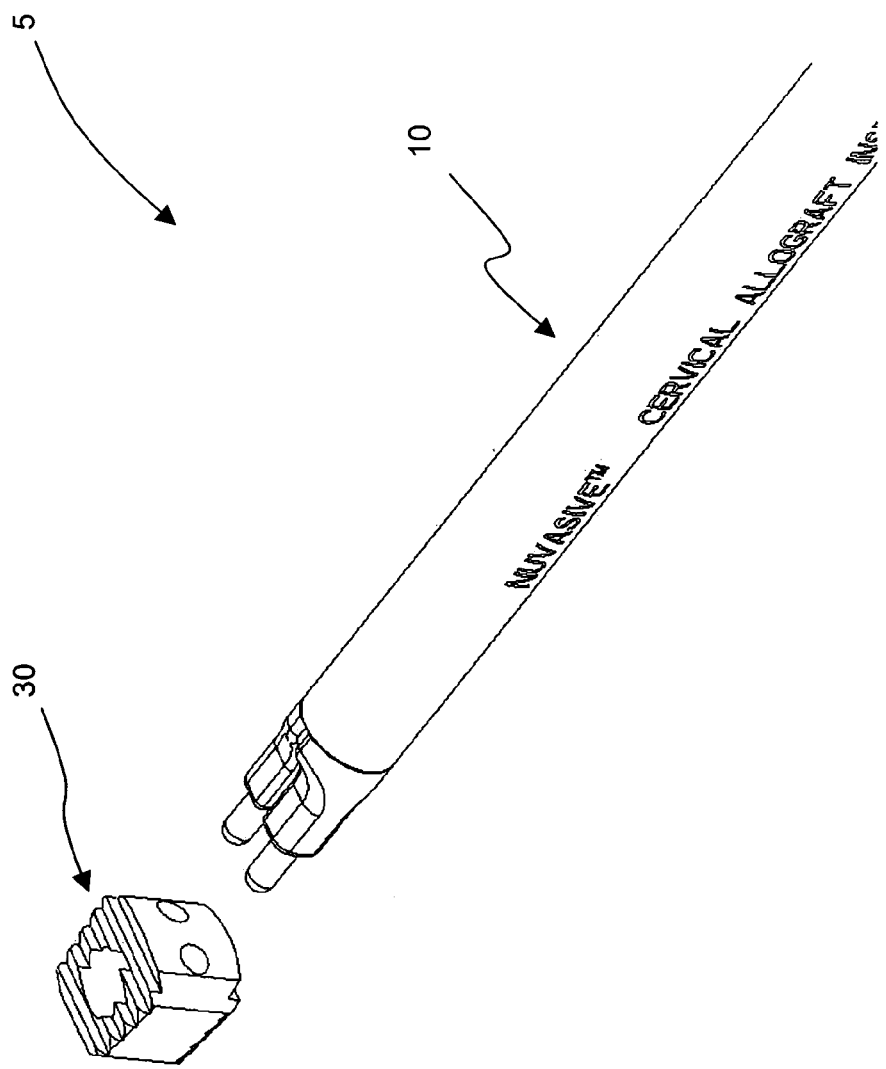
FIG. 2 is an enlarged perspective view of the distal region of the system shown in FIG. 1, detailing the attachment features between an exemplary implant and exemplary inserter assembly according to the present invention.
Figure 3:
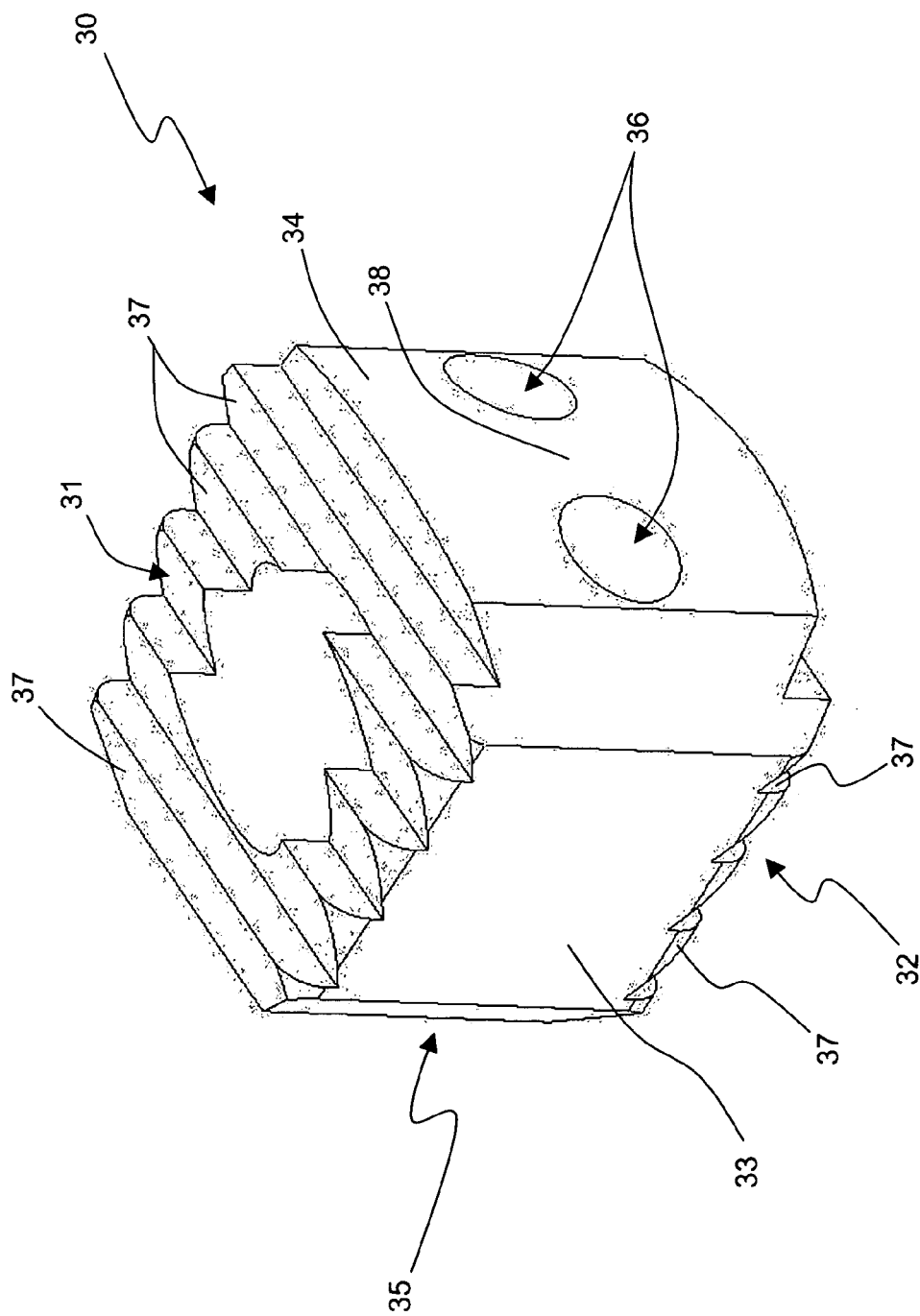
FIG. 3 is an enlarged perspective view of the exemplary implant shown in FIGS. 1–2.
Figure 4:
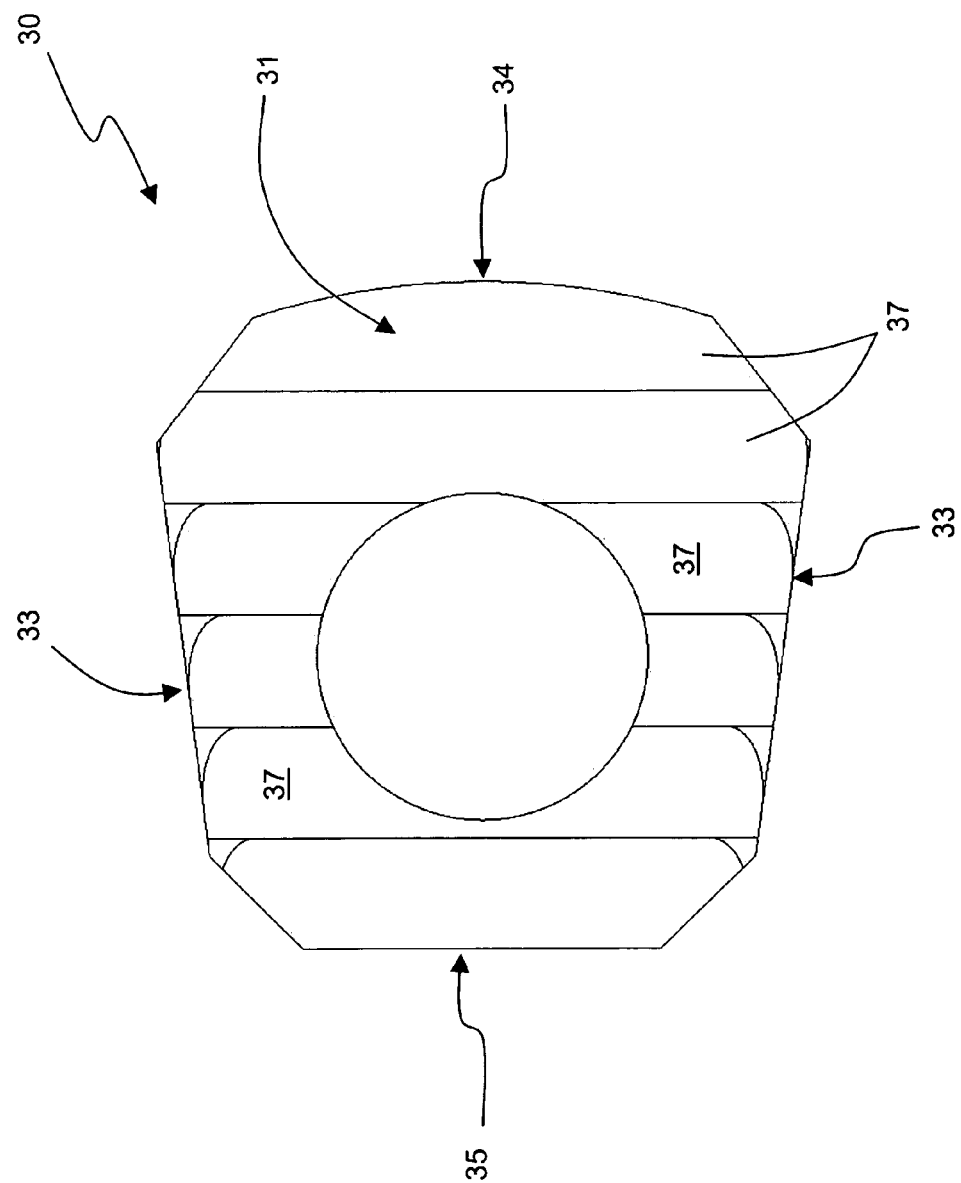
FIGS. 4–6 are top, side, and front views, respectively, of the exemplary implant shown in FIGS. 1–2 according to the present invention.
Figure 5:
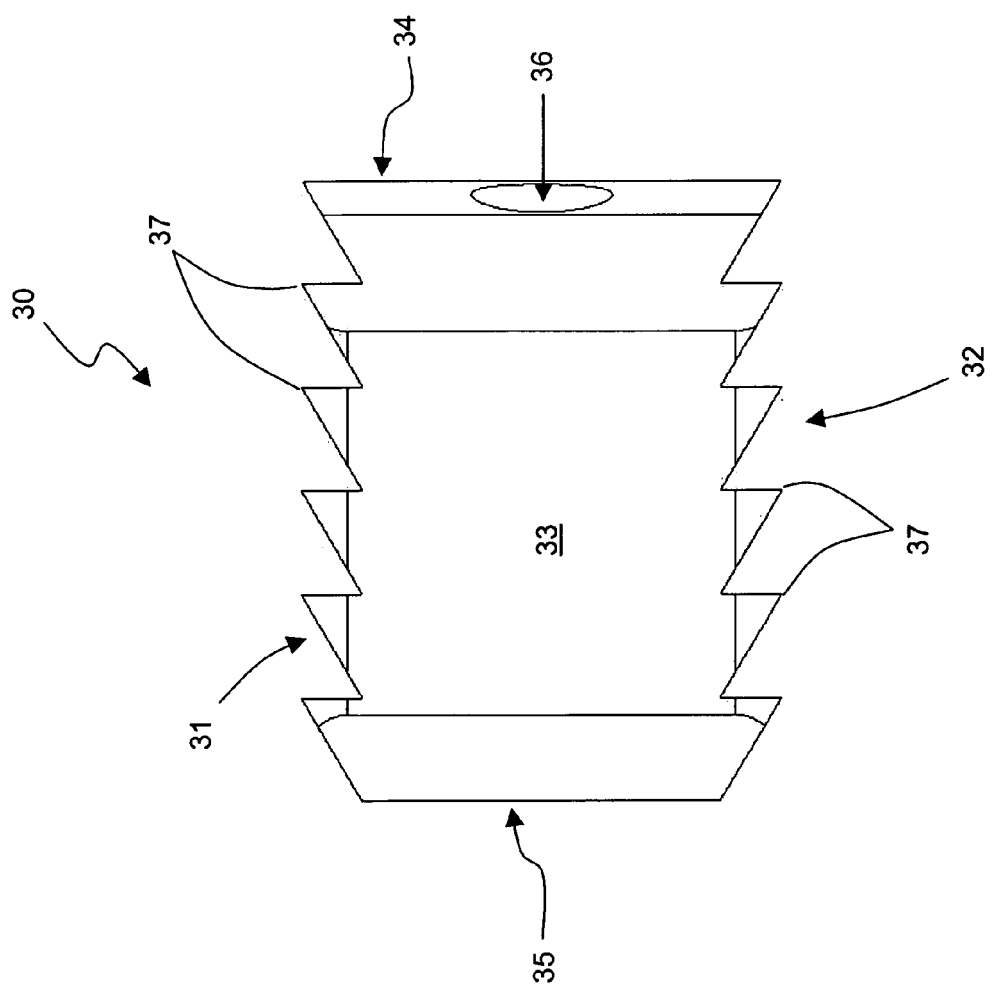
Figure 6:
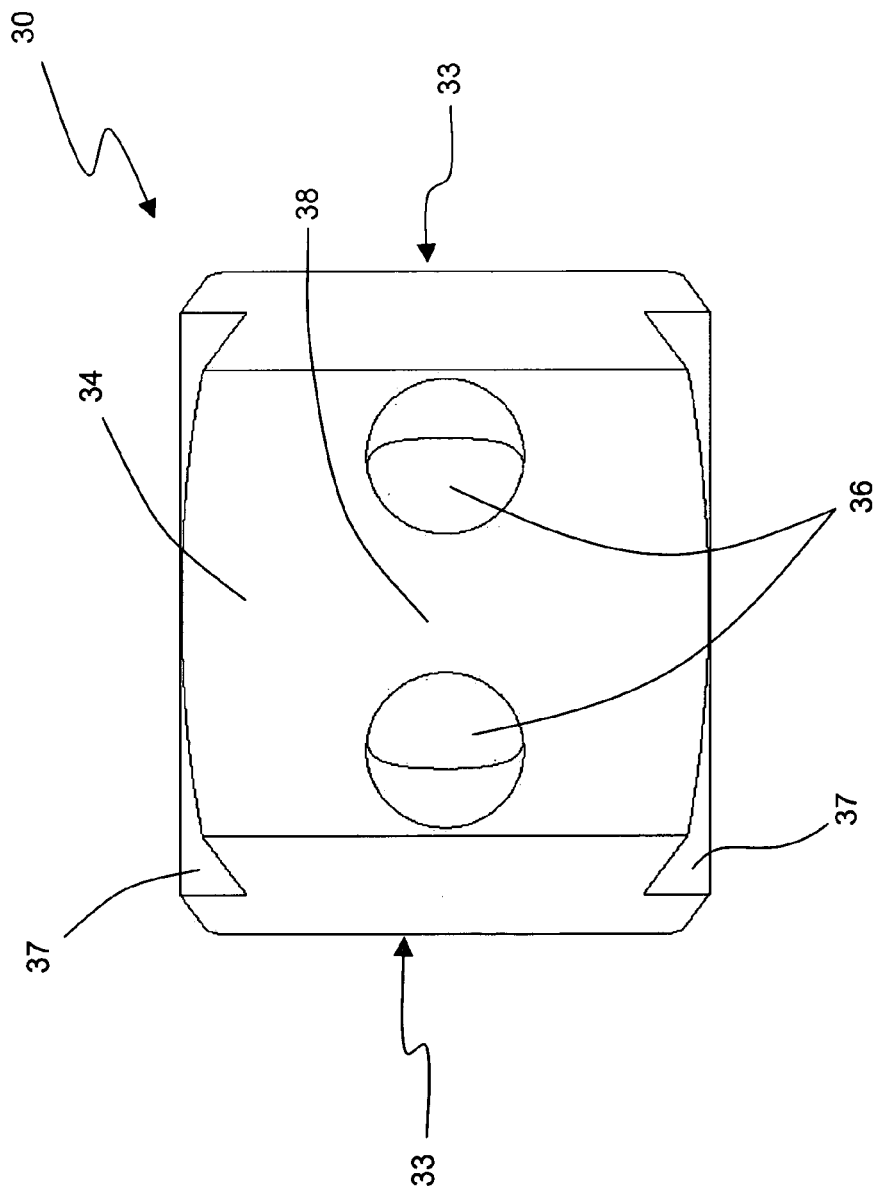

FIGS. 1–2 illustrate a system 5 for performing spinal fusion between adjacent cervical vertebrae, including an exemplary implant 30 and an exemplary inserter assembly 10 provided in accordance with the present invention. As will be described in detail below, the inserter assembly 10 is configured to releasably maintain the exemplary implant 30 in the proper orientation for insertion. The implant 30 may be simultaneously introduced into a disc space while locked within the inserter 10 and thereafter released. The exemplary implant 30, having been deposited in the disc space, effects spinal fusion over time as the natural bone healing process integrates and binds the implant with the adjacent vertebral bodies. This fusion may be facilitated or augmented by introducing or positioning various materials in a space created within or adjacent to the implant 30. Those materials may be introduced before, during, or after the insertion of the exemplary implant 30. The additional material may include bone autograft harvested from the patient receiving the implant 30, one or more additional bone allograft or xenograft implants, any number of non-bone implants, and any number of fusion promoting compounds such as bone morphogenic protein. While described below primarily with reference to the cervical spine, it is to be readily appreciated that the system for performing spinal fusion of the present invention may be suitable for accomplishing fusion in any spinal region (lumbar, thoracic, and cervical).

FIGS. 3–9 depict various embodiments of the exemplary implant 30. Some common attributes are shared among the various embodiments. More specifically, each implant 30 has a top surface 31, a bottom surface 32, lateral sides 33, a proximal side 34, and a distal side 35. In one embodiment, the top and bottom surfaces 31, 32 are generally parallel. The implants 30 preferably include two apertures 36 which are generally parallel to one another. The apertures 36 extend inwardly from the proximal side 34 in a generally perpendicular fashion relative to the proximal side 34. Although shown as having a generally circular cross-section, it will be appreciated that the apertures 36 may be provided having any number of suitable shapes or cross-sections, including but not limited to rectangular or triangular. The implant 30 includes a purchase region 38 extending between the apertures 36 for releasable engagement with the inserter assembly 10. The exemplary implant 30 also preferably includes anti-migration features along the top surface 31 and bottom surface 32 to increase the friction between the implant and the adjacent contacting surfaces of the vertebral bodies. That friction prohibits migration of the implant 30 during the propagation of natural bony fusion. In the exemplary implant 30, the anti-migration feature comprises a series of angular teeth 37 are disposed on the top 31 and bottom 32 sides.

Figure 7:
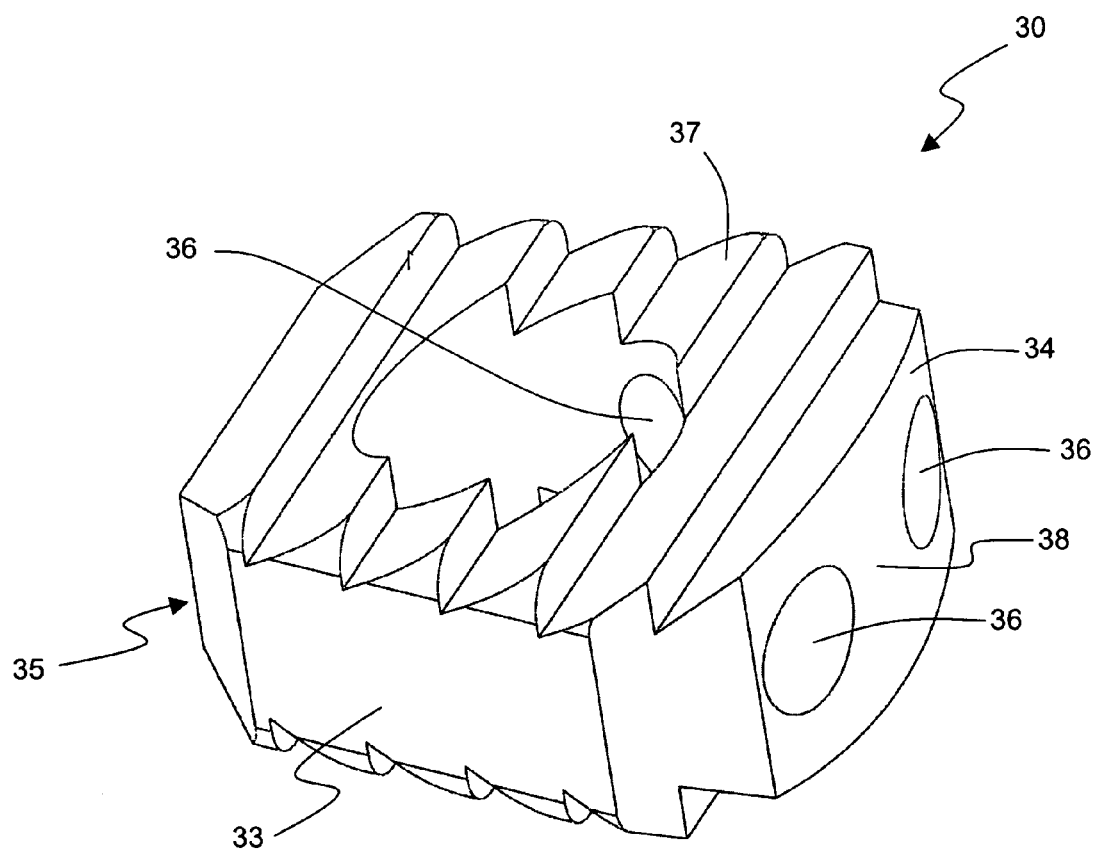
FIG. 7 is a perspective view of an exemplary implant having, by way of example only, a height of 5 mm, a width of 11 mm, and a length of 11 mm according to the present invention.
Figure 8:
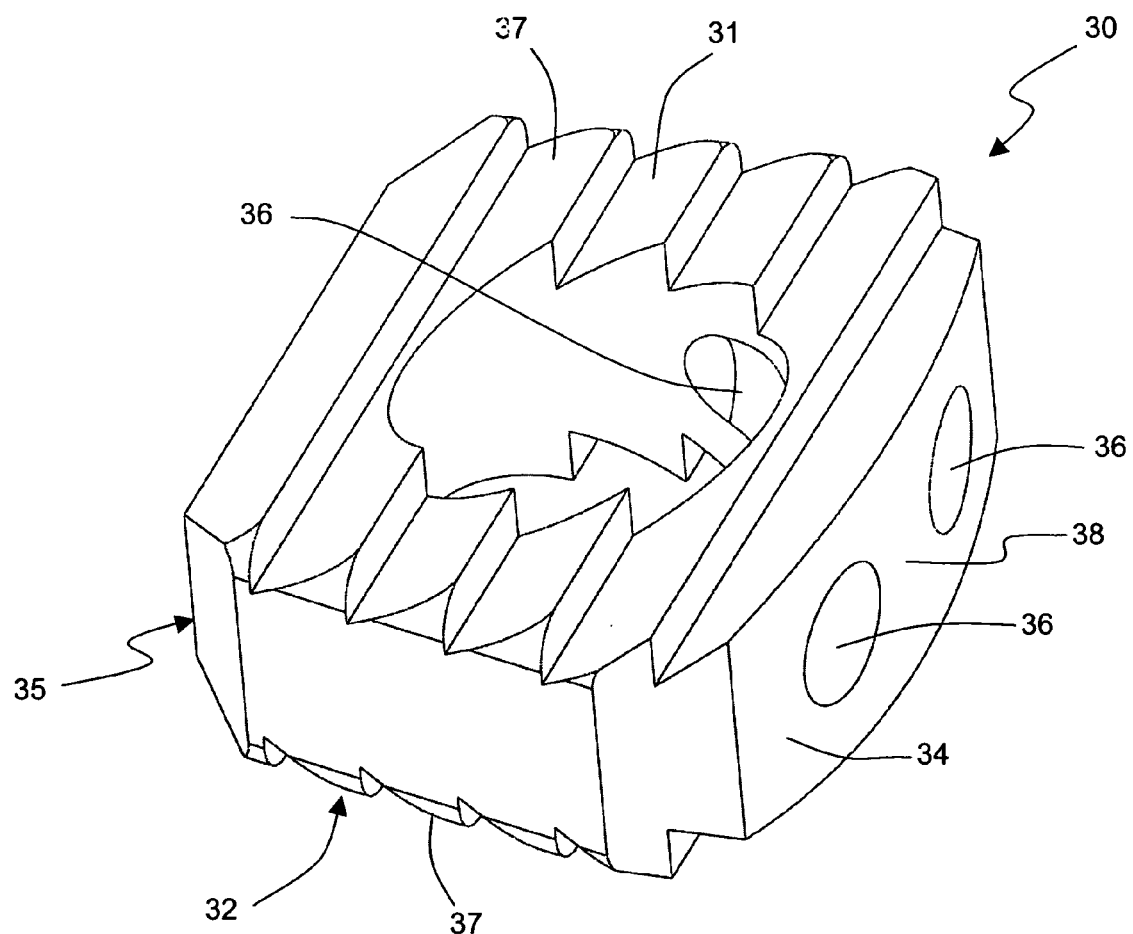
FIG. 8 is a perspective view of an exemplary implant having, by way of example only, a height of 5 mm, a width of 14 mm, and a length of 11 mm according to the present invention.
Figure 9:
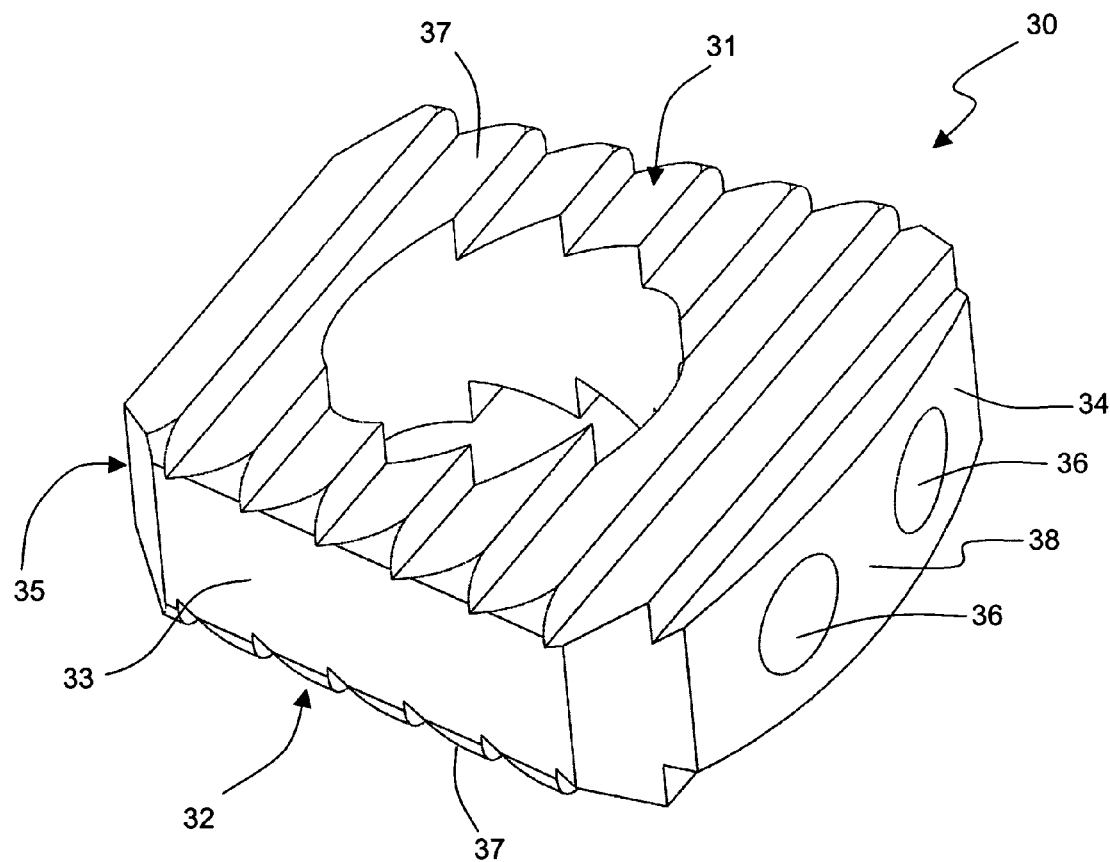
FIG. 9 is a perspective view of an exemplary implant having, by way of example only, a height of 5 mm, a width of 14 mm, and a length of 14 mm according to the present invention.
Figure 10:
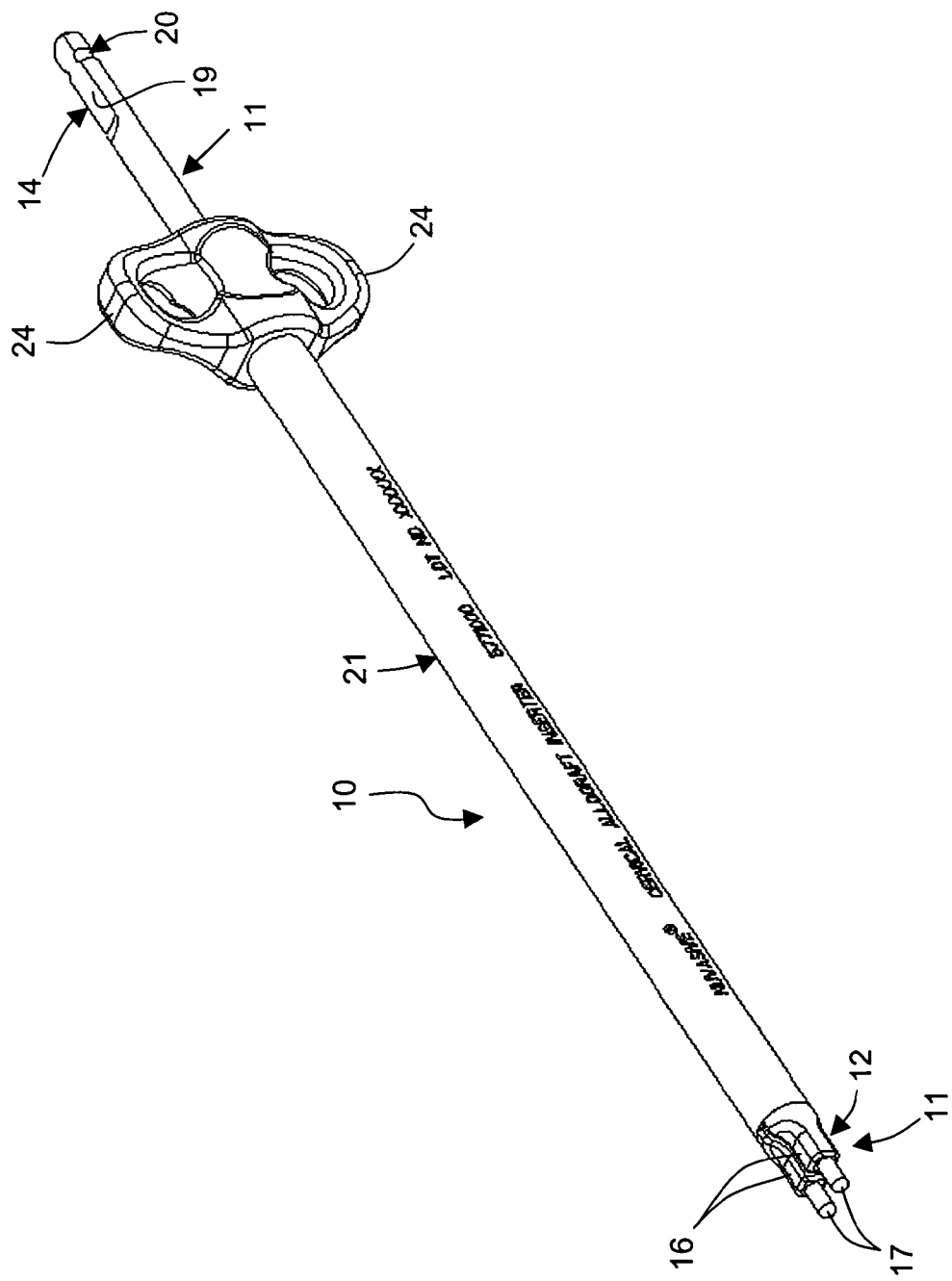
FIG. 10 is a perspective view of an exemplary inserter fully assembled, including an elongate fork member and a tubular lock member.
Figure 11:
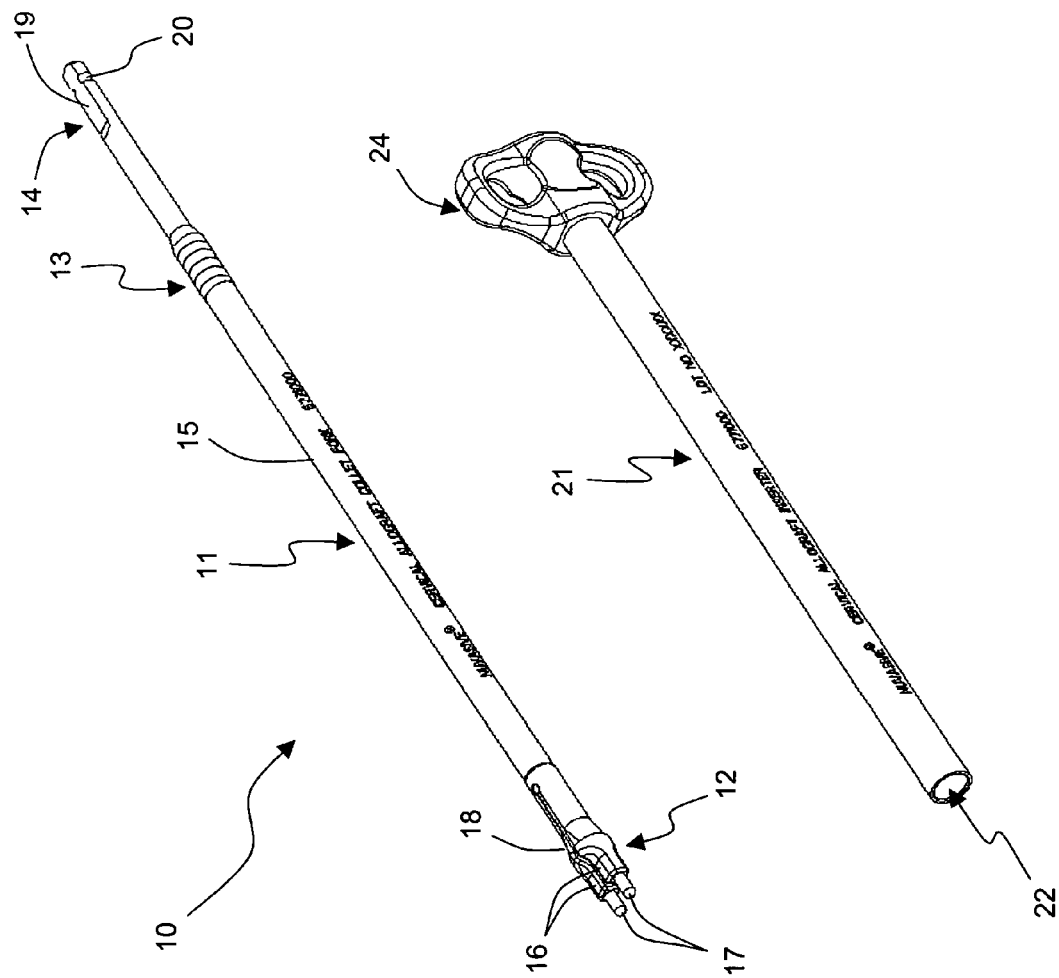
FIG. 11 is a perspective view of an exemplary inserter unassembled, including an elongate fork member and a tubular lock member.
Figure 12:
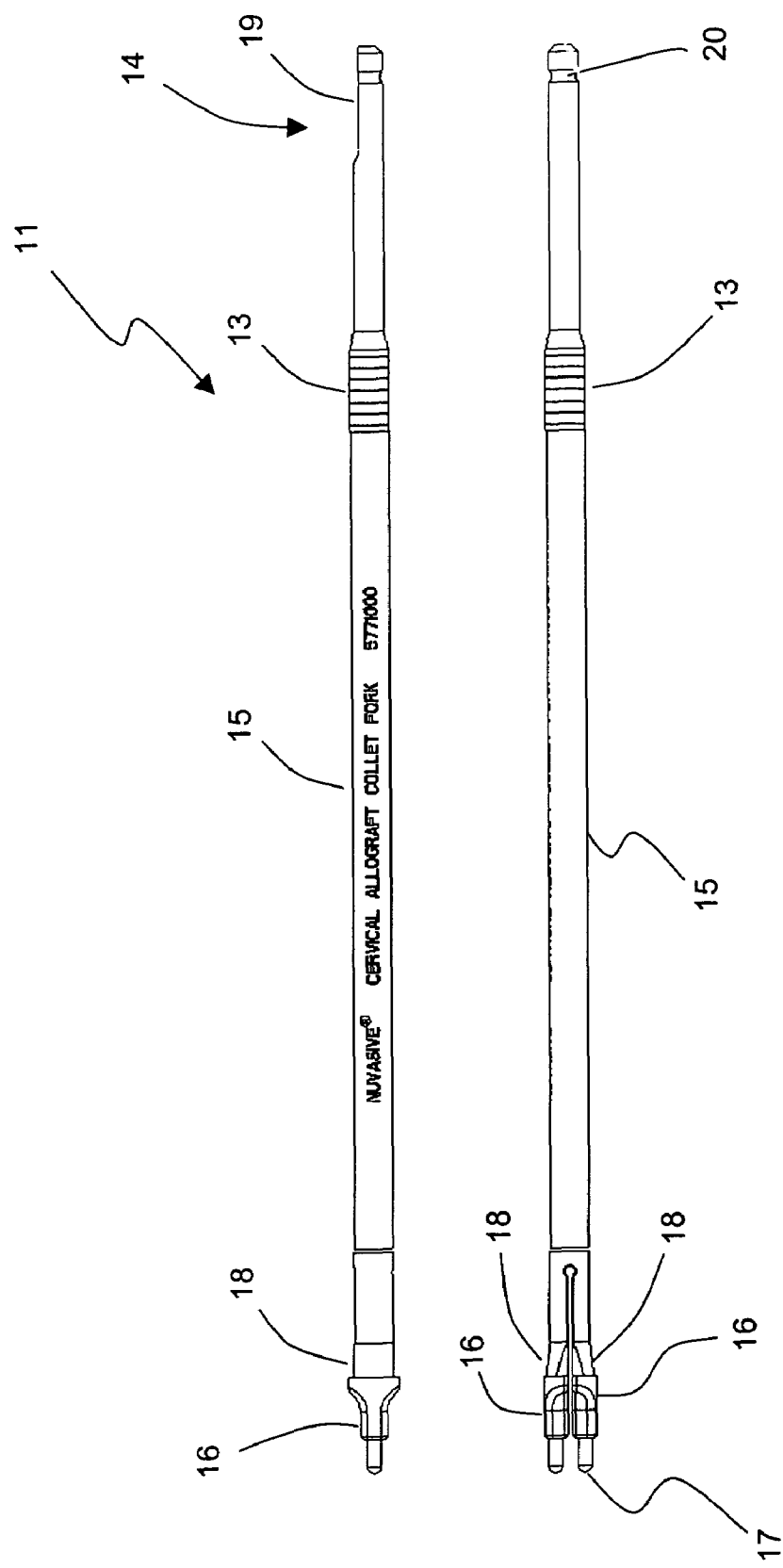
FIG. 12 includes a side view and a top view, respectively, of the elongate fork member of the inserter according to the present invention.

FIGS. 7–9 illustrate various embodiments of the exemplary implant 30. FIG. 7 depicts a 5 mm tall, 11 mm wide, and 11 mm long implant 30. FIG. 8 depicts a 5 mm tall, 14 mm wide, and 11 mm long implant 30. FIG. 9 depicts a 5 mm tall, 14 mm wide, and 14 mm long implant 30. Although each of the presented embodiments has a height dimension of 5 mm, it should be readily understood that the height of the implant 30 may range from approximately 2–12 mm. Alternatively, the top 31 and bottom 32 surfaces may be angled with respect to one another to match the natural curvature of the spine (i.e., lordosis or kyphosis). By way of example, implants designed for the cervical or lumbar regions of the spine will have anterior height greater than the posterior height to match the natural lordosis in those regions. Inversely, implants designed for implantation into the thoracic region will be manufactured with an anterior height dimension smaller than the posterior height to match the natural kyphosis in that region.

FIGS. 10–13 detail the exemplary implant inserter 10 according to one embodiment of the present invention. The exemplary inserter 10 includes an elongate fork member 11 and a tubular lock member 21. The elongate fork member 11 is constructed with a two-pronged feature 12 at its distal end, a thread feature 13 proximal of the two-pronged feature 12 and a handling feature 14 further proximal. The central portion 15 of the elongate fork member 11 (i.e., between the distal two-pronged feature 12 and the proximal thread feature 13) is generally cylindrical of a length sufficient to allow the device to span from the surgical target site to a location sufficiently outside the patient's body so the handling feature 14 can be easily accessed by a clinician or a complimentary controlling device.

The two-pronged feature 12 disposed at the distal end of the elongate fork member 11 utilizes two clamping arms 16. The clamping arms 16 are generally parallel and spaced apart from one another when in a freestanding configuration. An engagement feature 17 is disposed on each of the clamping arms 16 at its distal end generally parallel to the clamping arms 16. Each engagement feature 17 is coupled with the clamping arms 16 so that the engagement feature 17 is restrained from movement relative to the clamping arm 16. The engagement features 17 are generally cylindrical with a diameter smaller than the apertures 36 previously described on the exemplary implant 30 enabling each of the engagement features 17 to slidably engage one of the apertures 36.

Further proximal from the engagement features 17, the outer surface of each of the clamping arms 16 is tapered when the arms are in a freestanding parallel relationship to one another. The taper feature 18 is oriented with the larger dimension closest to the engagement features 17 and the smaller dimension closest to the proximal handling feature 14 of the device. Proximal to the taper feature 18, the elongate fork member 11 becomes generally cylindrical and has a constant diameter approximately matching the smallest outer dimension of the taper feature 18. In the presented embodiment, the clamping arms 16 join to form one body. The length of the generally cylindrical portion 15 ranges from approximately 2–23 cm. A threaded feature 13 is disposed concentric and proximal to the generally cylindrical portion 15.

The handling feature 14 in the exemplary embodiment is the most proximal feature and is generally cylindrical. The handling feature allows a clinician to manipulate the tool during an implant insertion procedure which may include multiple facets or knurling. Alternatively, the handling feature 14 may be constructed to engage a complimentary control device. In the presented embodiment, the handling feature 14 is generally cylindrical with one flat surface 19. In addition, a concentric channel 20 is disposed toward the proximal end of the handling feature 14 and intersects the flat surface 19. When mated to a complimentary handling device, the flat surface 19 restricts rotation between the complimentary handling fixture and the handling feature 14. Similarly, the concentric channel 20 provides a surface that may be engaged by a retractable feature on the complimentary handling fixture to restrict axial motion between the complimentary handling fixture and the elongate fork member 11.

Figure 13:
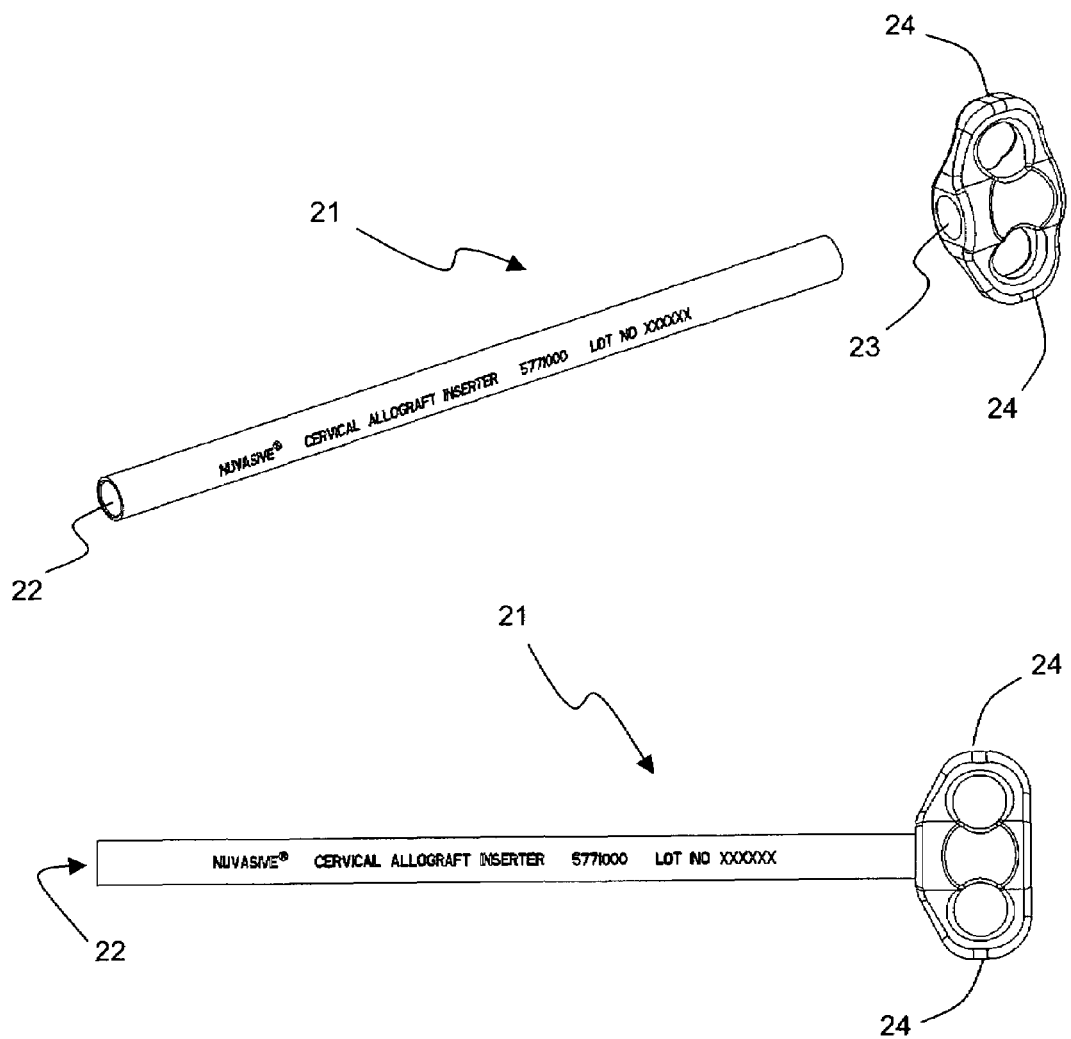
FIG. 13 includes a perspective view and a side view, respectively, of the tubular lock member of the inserter according to the present invention.

FIG. 13 details the tubular lock member 21 of the exemplary inserter 10. The tubular lock member 21 includes a central bore 22 dimensioned to receive the proximal end of the elongate fork member 11 therein. The internal dimension of the central bore 22 is smaller than the largest freestanding outer dimension of the taper feature 18. As a result, the portion of the elongate fork member 11 that may be received by the central bore 22 of the tubular lock member 21 is limited by interference between the distal end of the tubular lock member 21 and the taper feature 18 of the elongate fork member 11. In the presented embodiment, the outer dimension of the threaded feature 13 of the elongate fork member 11 is smaller than the largest outer dimension of the taper feature 18 on the elongate fork member 11. A thread feature 23 is located at the proximal end of the tubular lock member 21 that in the central bore 22. The thread feature 23 matches the thread feature 13 on the elongate fork member 11 so that they can be threadably attached to one another. To ease the rotation of the tubular lock member 21 by hand, two semi-circular wings 24 may be provided protruding laterally outward from either side of the tubular lock member 21. Alternatively, other methods of creating a gripping surface are contemplated including but not limited to knurling or facets.

In order to use the system to perform a spinal fusion procedure, the clinician must first designate the appropriate implant size. After the implant 30 is chosen, the engagement features 17 of the elongate fork member 11 are inserted into the apertures 36 on the implant 30. At that time the implant 30 and elongate fork member 11 are slidably engaged with one another. Before the clinician can manipulate the combined implant 30 and elongated fork member 11, they must be releasably secured together. In order to secure the implant 30 onto the elongate fork member 11, the clinician would next employ the tubular lock member 21. The clinician would insert the proximal end of the elongate fork member 11 into the central bore 22 of the tubular lock member 21 at its distal end. The tubular lock member 21 would then be advanced over the elongate fork member 11 until the thread feature 13 of that member and the thread feature 23 of the tubular lock member 21 become engaged.

Once engaged, advancement of the tubular lock member requires rotation of the tubular lock member 21 with respect to the elongate fork member 11. Preferably, after only a small amount of engagement of the thread features the distal end of the tubular lock member 21 would contact the taper feature 18 of the elongate fork member 11. The tubular lock member 21 would be advanced creating greater interference as the distal end approaches the distal end of the taper feature 18 which has the larger outer dimension. The increasing interference would laterally displace the clamping arms 16 of the elongate fork member 11 towards each other. Since the engagement features 17 of the elongate fork member 11 were initially inserted into the apertures 36 of the exemplary implant 30, the displacement of the clamping arms 16 would create a compressive force on the purchase region 38 separating the apertures 36 of the exemplary implant 30. That compressive force allows a clinician to manipulate the system without the exemplary implant 30 becoming disengaged from the inserter 10.

A clinician can utilize the secured system in either an open or minimally invasive spinal fusion procedure. In either type of procedure, a working channel would be created in a patient that reaches the targeted spinal level. After the creation of that channel, the intervertebral space would be prepared. After preparation the secured device is used to place a spinal implant 30 into the prepared intervertebral space. Once the implant 30 is inserted into the prepared space, the implant 30 is released from the implant inserter 10 by retracting the tubular lock member 21 from the elongate fork member 11 by rotating the tubular lock member 21 with respect to the elongate fork member 11 in the opposite direction from that used to initially secure the implant 30. That motion removes the compressive force on the purchase region 38 between the apertures 36 of the implant 30 and allows the engagement features 17 to be slidably removed from the apertures 36. After the engagement features 17 are disengaged from the implant 30, the inserter 10 is removed from the working channel and the channel is closed. As previously mentioned, additional materials may be included in the procedure either before, during or after the insertion of the implant 30 to aid the natural fusion of the targeted spinal level.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention as defined by the appended claims.

For example, although shown and described above with reference to implants formed from bone, it is to be readily appreciated that the insertion tool and manner of delivering multiple implants simultaneously may be employed with implants of any number of suitable constructions, including but not limited to metal, ceramic, plastic or composite. Moreover, with regard to bone, it will be readily appreciated that this term may be construed to include bone autograft (from the patient), allograft (from other human cadavers), or xenograft (bone from other species). It will also be appreciated that, although shown within the context of cervical spinal fusion, the system and related methods disclosed herein may find application in other areas of spinal fusion, such as thoracic and/or lumbar spinal fusion, such as may be accomplished by varying the sizes and dimensions of the implants and introducer system depending upon the particular spinal level (thoracic or lumbar). As an added convenience, the inserter 10 and/or any of a variety of sizer instruments used with the inserter 10 may be provided in a color-coded fashion comprising any number of different colors, with each color denoting a specific size implant 30 to employ. In this fashion, the surgeon may quickly and easily identify which size implant 30 (as well as a specific size inserter 10) depending upon the color coding of the sizer (not shown) employed to pre-size the intradiscal space.

What is claimed is:

1. An implant insertion device for inserting a spinal implant having at least two apertures defining a purchase region therebetween, comprising:

an elongate fork member having a pair of clamping arms extending generally parallel and away from the distal end of an elongate section, each clamping arm having an engagement feature dimensioned to slidably engage said apertures of said spinal implant, a thread feature at the proximal end of the elongate section and a generally cylindrical handling feature further proximal from said thread feature; and a generally tubular member having a distal end, a bore dimensioned to receive a proximal portion of said elongate fork member therethrough from the distal end but smaller than the outer dimension of said clamping arms of said elongate fork member and a thread feature at the proximal end that is dimensioned to engage said thread feature of said elongate fork member, whereby clockwise rotation of said tubular lock member with respect to said elongate fork member will cause said distal end of said tubular lock member to force said clamping arms of said elongate fork member to displace laterally toward the longitudinal axis of said elongate fork member, the lateral displacement causing said engagement features to displace toward each other securing said spinal implant by creating a compressive force on said purchase region.

2. The implant insertion device of claim 1, wherein said engagement features are generally cylindrical pins mechanically coupled to and generally parallel to said longitudinal axis of said tubular lock member.

3. The implant insertion device of claim 1, further comprising at least two wings protruding radially from the outer surface of said tubular lock member providing a surface to ease rotation of said tubular lock member.

4. The implant insertion device of claim 1, wherein said generally cylindrical handling feature further comprises at least one generally flat facet on said generally cylindrical handling feature, and at least one channel circumscribing said generally cylindrical handling feature.

5. A method for performing spinal fusion comprising using a spinal implant having at least two apertures and a purchase region therebetween and an implant inserter engaging said spinal implant by slidably engaging said apertures and creating compressive force on said purchase region, comprising:

providing a spinal implant having top and bottom sides, lateral sides, a proximal side and a distal side, said top and bottom sides having a generally polygonal shape, said proximal side being intersected generally perpendicular by at least two apertures creating a purchase region therebetween;

providing a spinal implant insertion device having an elongate fork member and a tubular lock member, said elongate fork member having a pair of clamping arms extending generally parallel and away from the distal end of an elongate section, each clamping arm having an engagement feature dimensioned to slidably engage said apertures of said spinal implant, a thread feature at the proximal end of the elongate section and a handling feature further proximal from said thread feature and said generally tubular lock member having a distal end, a bore dimensioned to receive a proximal portion of said elongate fork member therethrough from the distal end but smaller than the outer dimension of said clamping arms of said elongate fork member and a thread feature at the proximal end that is dimensioned to engage said thread feature of said elongate fork member;

engaging said at least two apertures of said spinal implant with said engagement features of said elongate fork member;

rotating said tubular lock member clockwise with respect to said elongate fork member causing said distal end of said tubular lock member to force said clamping arms of said elongate fork member to displace laterally toward the longitudinal axis of said elongate fork member, the lateral displacement causing said engagement features to displace toward each other securing said spinal implant by creating a compressive force on said purchase region;

introducing said inserter and said secured spinal implant into a prepared intervertebral space;

rotating said tubular lock member counterclockwise with respect to said elongate fork member causing a reduction of said compressive force on said purchase region and allowing said engagement features of said elongate fork member to be slidably disengaged from said spinal implant; and removing said spinal implant insertion device from said prepared intervertebral space.

6. The implant insertion device of claim 1, wherein at least part of the implant insertion device is color-coded to indicate to the surgeon which size implant insertion tool to use depending upon the size of the spinal implant.

7. The method of performing spinal fusion of claim 5, wherein at least part of the implant insertion device is color-coded to indicate to the surgeon which size implant insertion tool to use depending upon the size of the spinal implant.

* * * * *